United States Patent [19]

Ender et al.

[11] 4,169,470
[45] Oct. 2, 1979

[54] SURGICAL NAIL FOR USE IN SETTING BONE FRACTURES, AND TOOL FOR EMPLACING SAME

[76] Inventors: Josef Ender, Steinbrecherring 23, Steyr, Austria, 4400; Hans G. Ender, Ferstelgasse 6/20, Vienna, Austria, 1090

[21] Appl. No.: 843,531

[22] Filed: Oct. 19, 1977

[51] Int. Cl.² .............................................. A61F 5/04
[52] U.S. Cl. ........................... 128/92 BC; 128/92 EC
[58] Field of Search ............ 128/92 BC, 92 EC, 92 B, 128/92 BA, 92 R, 83

[56] References Cited

U.S. PATENT DOCUMENTS

| | | | |
|---|---|---|---|
| 2,998,007 | 8/1961 | Herzog | 128/92 BC |
| 3,709,218 | 1/1973 | Halloran | 128/92 BC |
| 3,779,239 | 12/1973 | Fischer | 128/92 BC |
| 4,055,172 | 10/1977 | Ender | 128/92 BC |

FOREIGN PATENT DOCUMENTS

| | | | |
|---|---|---|---|
| 735333 | 4/1943 | Fed. Rep. of Germany | 128/92 EC |
| 960010 | 10/1949 | France | 128/92 B |
| 118595 | 4/1947 | Sweden | 128/92 EC |
| 1022328 | 3/1966 | United Kingdom | 128/92 EC |

*Primary Examiner*—John D. Yasko
*Attorney, Agent, or Firm*—Otto John Munz

[57] ABSTRACT

An elongated relatively thin, elastic, flexible and resilient nail which, before emplacement in and along the medullary canal of a fractured bone, has a generally curved or arcuate form so that when flexed and stressed by insertion into and along the canal, its pointed proximal end may be facilely directed into the canal of the superjacent fragment, and finally into the trochanter. By turning the nail during emplacement the proximal end may be employed to rotate and adjust the bone fragments into correct or normal relation for healing. A tool or set is detachable connectable with the distal end of the nail, to facilitate emplacement and removal thereof.

24 Claims, 22 Drawing Figures

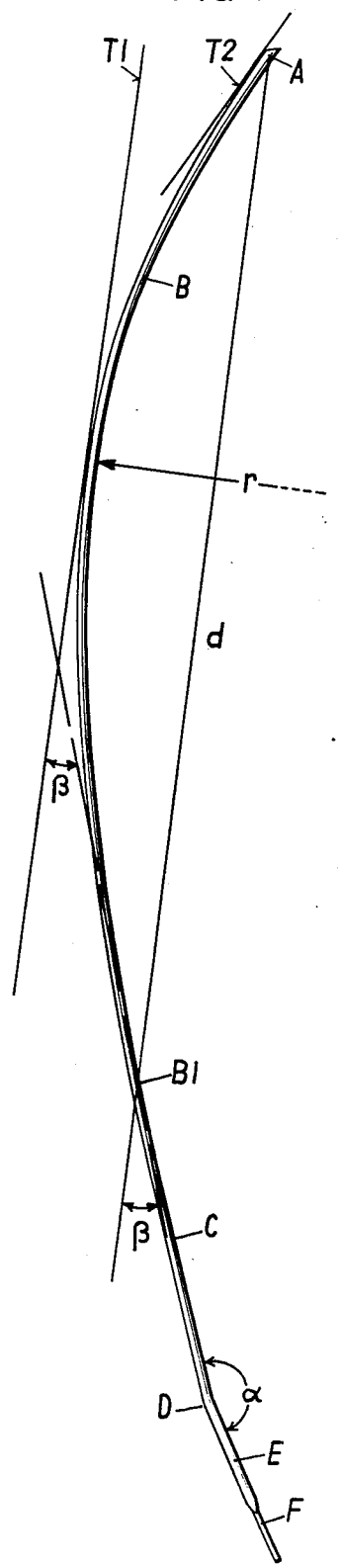
FIG.1
FIG.2
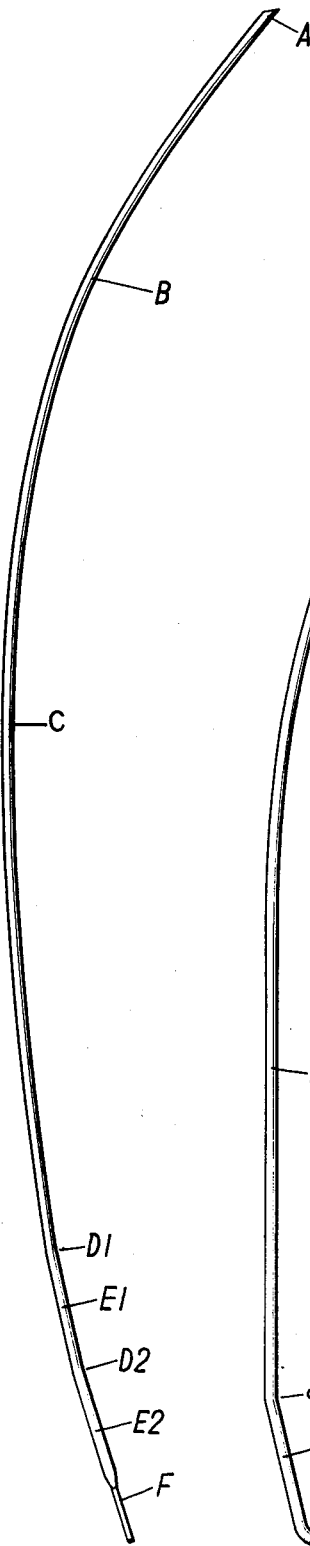
FIG.11
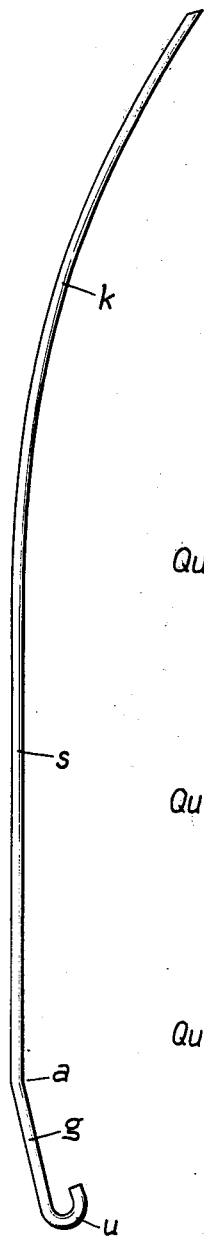
FIG.12
FIG.13a
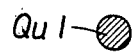
FIG.13b
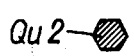
FIG.13c
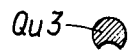

SURGICAL NAIL FOR USE IN SETTING BONE FRACTURES, AND TOOL FOR EMPLACING SAME

CROSS-REFERENCE TO RELATED APPLICATIONS

Priority of corresponding Austrian patent application No. A 6344/73, filed July 18, 1973 under Convention, the filing date of the corresponding U.S. patent application Ser. No. 477,418, filed June 7, 1974, abandoned Apr. 22, 1975, and U.S. patent application Ser. No. 568,987, filed Apr. 17, 1975, now U.S. Pat. No. 4,055,172, issued Oct. 25, 1977, is claimed as to all subject matter in common with the present application.

FIELD OF THE INVENTION

The invention relates to a surgical implement including a nail for the setting of fractured bones such as the radius or tibia, and in particular the femur. By skilled use of the invention the surgeon is enabled to insert the nail through an incision in the lower or distal end of the bone, to pass its pointed proximal end along the medullary canal of the fractured parts, to relatively adjust the parts rotationally and/or transversely until they are in normal relation, and to secure the parts in such relation for proper knitting, as by entering the proximal end into a trochanter adjacent the corresponding end of the bone. The nail embodying the invention is relatively thin, flexible, elastic and resilient so that a plurality of them may be employed as determined by the surgeon, in a bone to thus assure that the fractured parts are firmly held in adjusted relation until knitted, and then withdrawn. Since only a single relatively simple incision is required, the invention is relatively simple to emplace.

The invention also comprehends a nail as described in the preceding paragraph, in combination with a special tool or set temporarily connectable with the distal end of the nail, for use in driving the same in and along the medullary canal and at the same time being operable to angularly adjust the nail relatively to the bone as and for purposes subsequently described.

DESCRIPTION OF THE PRIOR ART

Nails and like devices for emplacement in the medullary canal of fractured bones, for maintaining the parts in correct relation during knitting, are known.

Halloran, U.S. Pat. No. 3,709,218, Jan. 9, 1973, is one example. The device disclosed by this patent is a rigid metal rod pre-shaped to conform to the shape of the particular bone to be repaired, and of cross-sectional size to occupy, when emplaced, substantially the entire medullary canal. Consequently nearly all of the bone marrow must be broached while, for obvious reasons, the rod must be driven in, in highly accurate angular relation with respect to the bone; and it cannot be angularly adjusted within the canal, once emplaced therein.

Another prior art device is shown by Fischer et al., U.S. Pat. No. 3,779,239, Dec. 18, 1973, showing a complicated structure including a rigid tube or sleeve pre-shaped to conform to the normal shape of that particular bone. At its distal end the tube carries an expansible section. When the tube and its expansion section are driven into the bone canal through an incision at the proximal end thereof, a rod in inserted into and along the tube, then threadedly attached to the terminal expansion section. Turning of the rod further then causes the expansion of the section to anchor the device within the bone. The device thus shown is complicated and expensive. During emplacement lateral thrust engendered by turning of the flexed rod, tends to cause undesirable transverse movement of the fractured parts due to tendency of the tube to shift or turn in and with respect to the medullary canal. The expense and difficulty in storage of the large number of such devices necessary to service any fractured bone of the body, are clear.

Herzog, U.S. Pat. No. 2,998,007, Aug. 29, 1961, teaches a stiff rigid steel tube open at both ends and pre-shaped if required by the contour of the particular bone to be repaired. The tube is longitudinally slotted at spaced locations along its length. Once emplaced, through an incision at the proximal end of the bone, spring wires are pushed into and through the tube and manipulated so that their ends project from appropriate ones of the slots to become anchored in the cancellus. Thus the patented device is relatively complicated, difficult to instal and properly manipulate. Apparently it immobilizes the patient's joint at the proximal end of the bone.

Rush, U.S. Pat. No. 2,579,968, Dec. 25, 1951, discloses a nail of flexible, resilient material and which is originally straight except for a slight curve or bend at its forward sharpened end. The particular feature taught by the patent resides in the shape of the sharpened distal end, by which that end, in penetrating the medullary canal, is cammed free of the cortex during movement therealong.

Other art deemed of lesser importance are:
German Pat. No. 735,333, (1943)
Swedish Pat. No. 118,595, (1947)
French Pat. No. 960,010, (1949)
British Pat. No. 1,022,328, (1966)

All art cited is believed classified in class 128, subclass 92.

The instruments taught by the prior art above noted are either solid, rigid rods pre-shaped to fit the contour of the medullary canal of a particular bone, and hence incapable of effecting a fine lateral and/or rotational relative adjustment of the fractured parts to restore them to normal relation, or, if flexible and resilient, are not pre-shaped as by sequential arcuate and straight portions to enable the surgeon by manipulation of the nail itself, to restore the fractured parts to normal relation. By the foregoing sentence it is understood that the inventive nail has resiliency such that while it may be flexed and stressed in a desired manner, by the mere act of insertion in and along the medullary canal of a fractured bone, it will when withdrawn from the canal, resume the pre-shaped form it had prior to insertion or emplacement.

SUMMARY OF THE INVENTION

The present invention differentiates over known prior art in providing a surgical nail which is relatively thin, flexible and resilient or elastic and which, prior to emplacement in and along the medullary canal of a fractured bone, is permanently shaped to define successive arcuate and straight portions, which enables the surgeon not only to ensure that the nail facilely traverses the medullary canal of the fractured parts, in succession, but also by angular movement of the nail, to relatively adjust the parts into their correct or normal relation, and finally to locate the nail in fixed relation to the bone, to thus hold the parts firmly thus promoting osteogenesis.

The principal objects of the invention are, therefore:
1. To provide a surgical nail which enables the restoration to normal relation, of the fractured parts of a bone, and their fixation in such relation during osteogenesis;
2. To provide a nail of the type aforesaid which is of particular utility in the relative adjustment and correct fixation of petrochanterous and subtrochanterous fractures of the femur;
3. To provide a nail as in the preceding paragraph, which may be emplaced by driving its proximal end upwardly through a small incision at the condyle;
4. To provide a nail as in the preceding paragraph, so constructed and shaped that by its rotation in and with respect to the medullary canal, its proximal end may be accurately passed in succession through the canal of the fractured parts, even though relatively offset, and those parts relatively transversely and rotationally adjusted back to normal relation;
5. To afford a nail as aforesaid which, when driven into final emplaced position, acts to hold the parts in correct relation for healing;
6. To provide the combination with a nail as in the preceding paragraphs, of a driving tool or set which is positively but releasably coupled or connected with the distal end of the nail and which enables it to be facilely driven into and along the medullary canal while being simultaneously rotated or angularly adjusted, as required for correct emplacement;
7. To provide a nail of the type afroesaid which is relatively thin, resilient, flexible and elastic and, while very effective for its intended purposes is nevertheless simple and inexpensive so that it is practicable to maintain on hand a supply of nails of different lengths, sizes and contours to encompass all elongated bones having medullary canals.

Other objects and advantages will become obvious to those skilled in the art, after a study of the following detailed description, in connection with the accompanying drawing.

BRIEF DESCRIPTION OF THE DRAWING

FIG. 1 is a front elevational view of the nail embodying the invention;

FIG. 2 is a view taken in a plane normal to that of FIG. 1;

FIG. 11 is a view corresponding to FIG. 1 but showing a nail of modified shape;

FIG. 12 is a view corresponding to FIG. 1, of a nail generally shaped like FIG. 1 but of lesser length than that of FIG. 1, and having a reversely bent distal end;

FIGS. 13a, 13b and 13c show different cross-sectional shapes which a nail embodying the invention may have;

DESCRIPTION OF THE PREFERRED EMBODIMENTS

Referring to FIGS. 1 and 2, the nail has its proximal end a cut at an angle of about 45° to its longitudinal axis at that location, to form a point which as shown, is disposed in the plane of curvature. From end A the nail has a steeply curved portion B, passing fairly and smoothly into a portion C which may be essentially straight or of much greater radius of curvature than portion B. Near its distal end the nail is bent at an obtuse angle D, followed by a relatively short straight portion E with flattened end F. FIG. 2 shows that the flat is pierced with a slot G.

Figure 3:
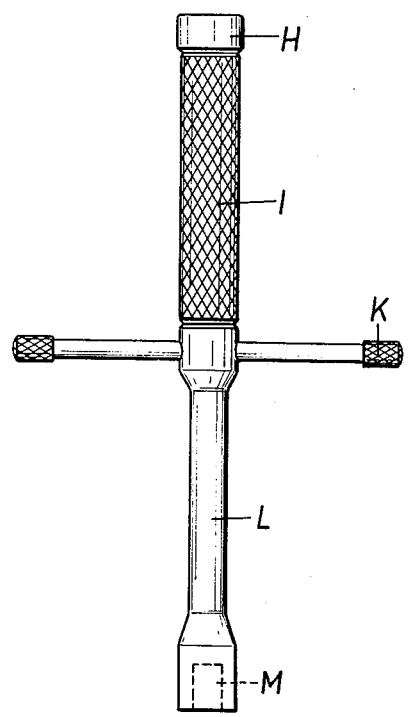
FIG. 3 shows a nail setting tool adapted for detachable connection with the nail of FIGS. 1 and 2.

FIG. 3 shows a nail set for use with the nail or splint of FIGS. 1 and 2. The lower end of shank L is enlarged and formed with a flattened cavity M sized for a smooth fit over flattened end F, FIGS. 1 and 2. By means of a knurled upper shank portion, head H and transverse lever K, the set may be used to drive the nail through an incision and into and along the medullary canal of a fractured bone while, if required, effecting rotational or angular adjustment thereof. Comparison of FIGS. 1 and 2 shows that the nail there shown in curved and/or bent in one plane only.

The nail of FIG. 11 is shaped essentially like the one of FIGS. 1 and 2, but has two successive bends D1 and D2 near its distal end, with a straight section E1 interposed therebetween. As in FIG. 1 the second bend D2 is followed by a third straight portion E2 with flattened end F.

FIG. 12 shows a nail somewhat shorter than those of FIGS. 1, 2 and 11. From its sharpened proximal or upper end this nail extends in an arc k of somewhat greater radius of curvature. The more steeply curved part merges smoothly into a medial portion s which may be straight or of relatively large radius so as to be more gently curved. At a the nail is bent toward the centers of curvature, followed by a relatively short straight section g terminating in a reversely bent or hooked end u. This affords means by which the nail may be engaged by the contiguous end of a set and driven into, or extracted from, the medullary canal. It will be understood that hooked end u may be replaced when desired, with a flat such as F, FIG. 11, as a matter of design.

Figure 10:
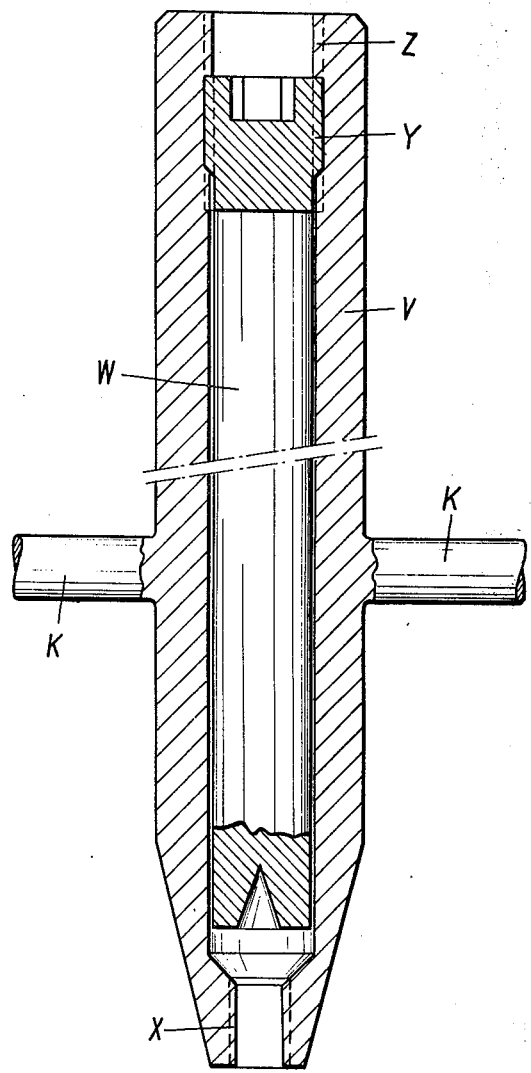
FIG. 10 is an axial broken section through a set constructed for connection with the distal end of the nail of FIG. 9.
Figure 9:
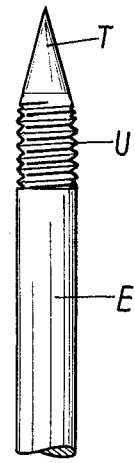
FIG. 9 is a detail view to an enlarged scale, of the distal end of a second embodiment of nail, adapted for threaded connection with a nail set.

FIG. 9 shows the distal end of a modified connection means wherein the nail has a pointed end T and screw threads U, followed by straight section E. See also FIG. 1. The set shown at FIG. 10 is constructed for use with the nail of FIG. 9. A tubular shank V is reduced at its lower end and internally threaded at X for engagement with threads U. A piston or plunger W fits the tubular interior of the shank. Its lower end is conically recessed as shown, to at times receive and fit over end T of the nail. The outer end of shank V is internally threaded to receive threaded abutment Y axially recessed to accept an Allen-head wrench. When the abutment is backed off the set may be threaded onto the end U of the nail. Then the abutment can be turned down until its conical recess receives and firmly grips the pointed end of the nail. In this manner the two are positievley coupled so that the set can be used to force the nail toward and into emplaced position, to retract it, and/or to angularly adjust it, as the surgeon deems requisite.

Figure 6:
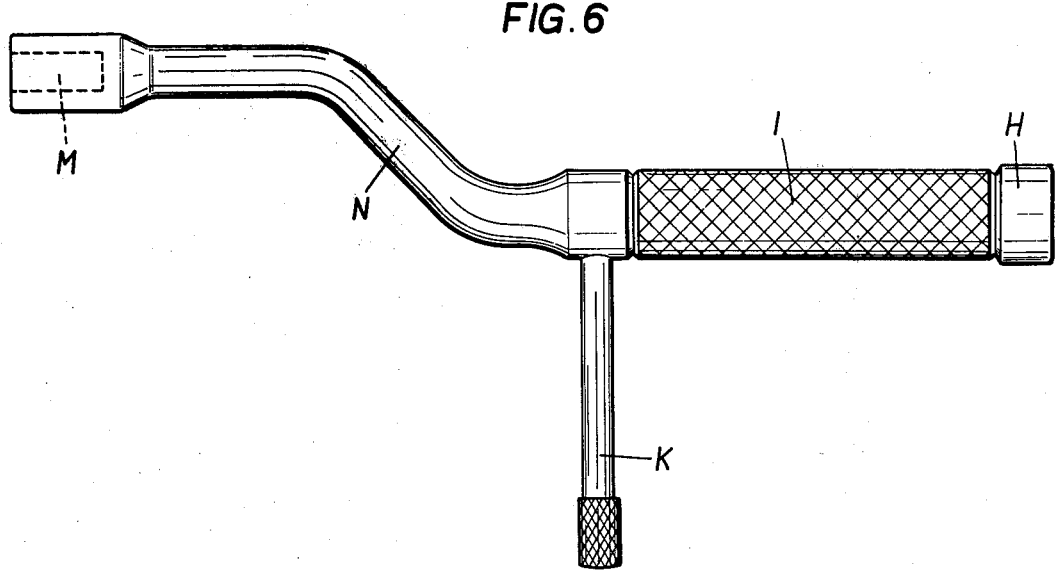
FIG. 6 is an enlarged front elevation showing a second embodiment of nail set.

FIG. 6 shows a form of nail set having an offset shank N, but operating in the same manner as the one shown at FIG. 3. Consequently it is thought sufficient to identify flattened recess M in the end of the shank, to non-rotatably receive flat F of a nail such as the one shown upon FIG. 1, knurled portion I, striking head H and crank or lever K. The offset shank has been found to promote or facilitate angular or rotational adjustment of a nail being emplaced.

Figure 7:
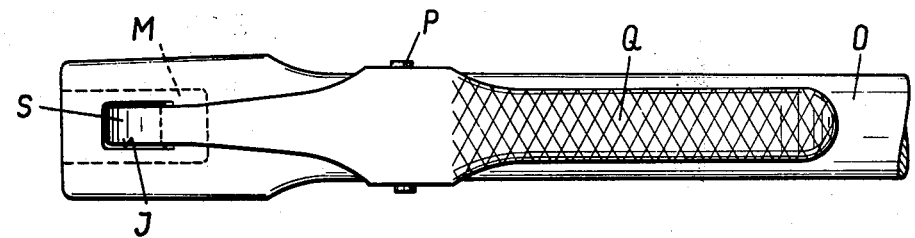
FIG. 7 is a detail view to a still further enlarged scale, showing the end of a third embodiment of nail set, for connection with the distal end of a nail like the one depicted upon FIGS. 1 and 2.
Figure 8:
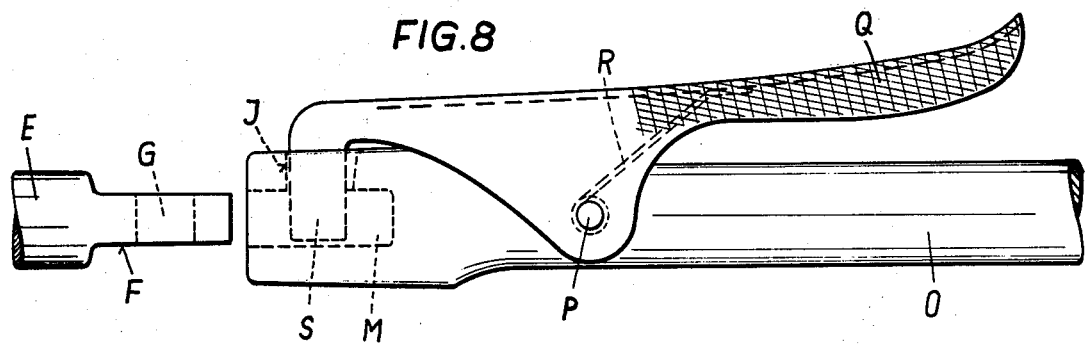
FIG. 8 is a view taken in a plane at right angles to that of FIG. 7, with the distal end of a nail about to be inserted into the cavity of the set.

FIGS. 7 and 8 disclose a form of set rapidly and positively connectable to the end F of a nail the distal end of which is illustrated at FIG. 8. In this modification of set, shank O has an enlarged end with flattened recess M for a smooth fit over and about flat F of the nail and its slot G. In addition, the end of the set has a radial slot J opening into recess M. A lever Q is pivoted by shaft P to the shank O, for movement about an axis normal thereto. The lever is formed with a nose S urged into the slot J by a spring R, in a way clear from inspection of FIG. 8. Thus, when shank O is grasped and the knurled portion of the lever is pressed, the nose is thereby moved out of slot J so that the flattened end of nail F can be moved into recess M to a position in registration between slots G and J. Then when lever Q is released, spring R moves the nose of the lever into the registered slots thus positively but releasably coupling the two items so that the set may be manipulated to emplace, withdraw and angularly adjust the nail, as and for the purposes described in connection with FIGS. 9 and 10.

Figure 18:
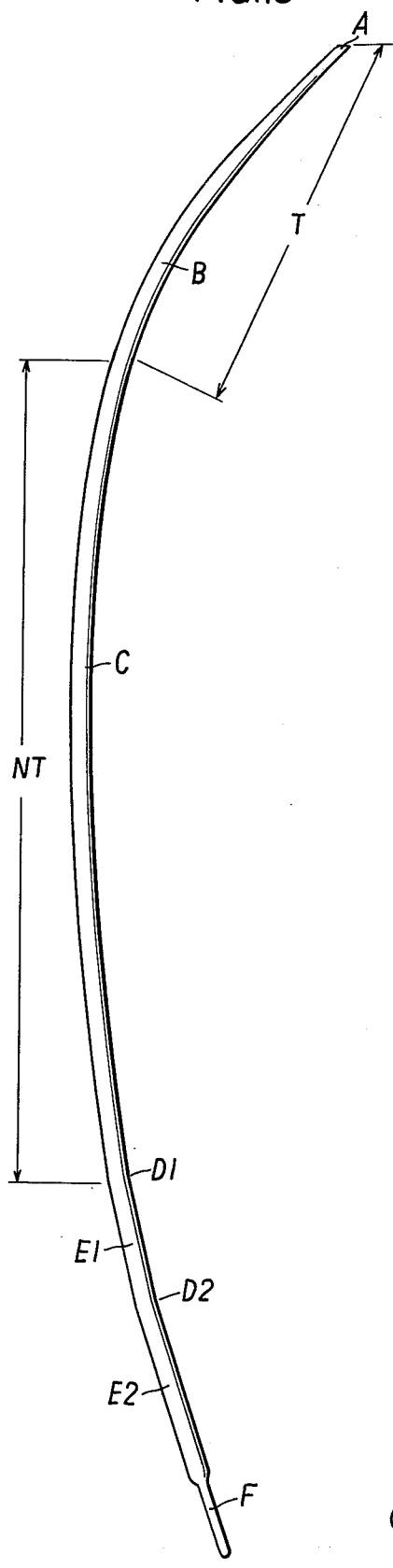
FIG. 18 is a view corresponding generally to FIG. 1 but showing a form of the invention wherein the cross-sectional area decreases slightly along the proximal end.

FIG. 18 shows a nail of the same general form as that of FIG. 11, including a flattened distal end and, if desired, the slot F, bends at D1, D2, with interspersed straight sections E1, E2. In this form of the invention the nail is gradually reduced in diameter over a distance indicated by chord T, from its proximal end to a distance of about 25% of the total or over-all length of the nail, measured along the nail rather than along the chord. From this ternminus, portion C, identified by chord NT and extending to bend D1, may have a length equal to about 50% of the over-all length of the nail. The lengths of straight portions E1, E2 may be about 10% and 15% of the over-all length, measured along the nail.

Figure 19:
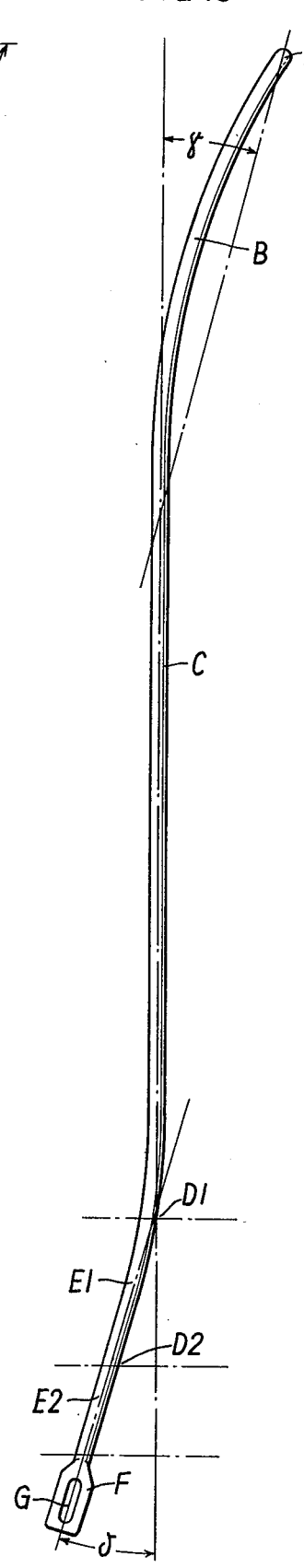
FIG. 19 shows a nail curved in a plane corresponding to the plane of FIG. 2.

FIG. 19 illustrates a modification wherein a nail such as the one depicted upon FIG. 1, is additionally curved in a second longitudinal plane normal to that of FIG. 1, that is, the nail is curved in two mutually normal longitudinal planes. The shape or form of this modification, in the plane of FIG. 1, is retained as indicated by the bends D1, D2 and interposed straight sections E1, E2. Still referring to FIG. 19, the angle $\gamma$ defined by a line forming a continuation of the straight portion C, and a chord extending from about the junction of the straight portion C and curved portion B, to the proximal end of the nail, may be from about 5° to 20°. The angle $\delta$ indicated upon FIG. 19, between the extended axis of portion C and its intersection at D1 with the nail axis between points D1 and end F, is about in the same range as the angle $\gamma$.

Figure 20:
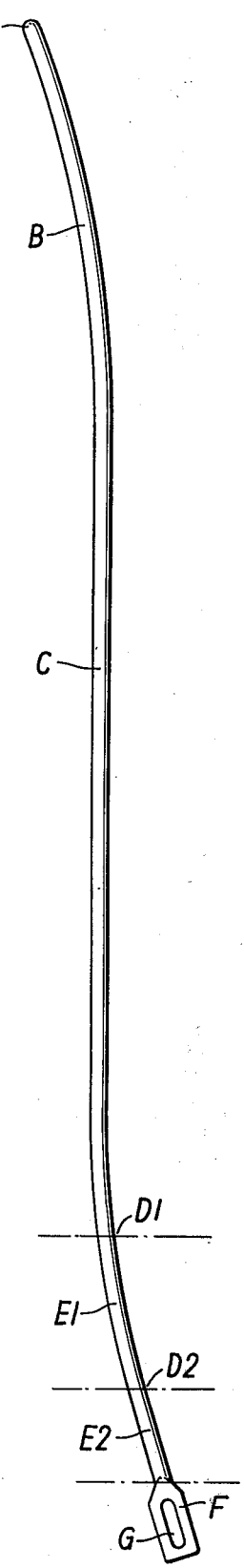
FIG. 20 displays a nail like FIG. 19 but having a somewhat greater radius of curvature at its proximal end.

FIG. 20 shows the nail of FIG. 19 rotated 180° about the axis of its straight portion C.

Figure 4:
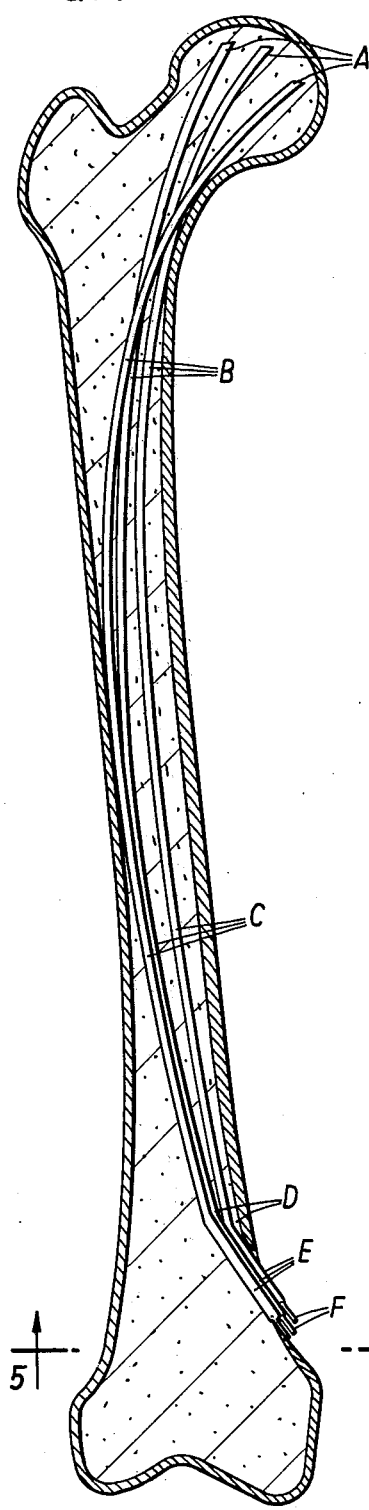
FIG. 4 is a longitudinal section taken in a plane through the central axis of a femur and showing the final emplaced positions of a plurality of nails such as that depicted upon FIGS. 1 and 2.

FIG. 4 illustrates the utility of the invention in repair of a femur. A relatively small incision is made at the distal end adjacent the condyle, and nails as illustrated upon FIGS. 1, 11, 18 or 19, are successively driven through the incision, upwardly in and along the medullary canal until finally emplaced with their proximal ends A within the trochanter and their flattened distal ends F disposed compactly contiguous to the cortex at the incision. The figure shows clearly how a plurality, in this case three, of the nails may cooperate to strengthen and reinforce a bone such as the femur, to promote and hasten osteogenesis.

Figure 5:
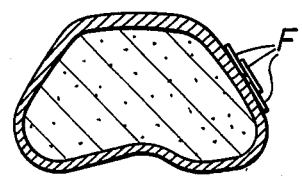
FIG. 5 is a transverse section taken in a plane about as indicated by line 5—5, FIG. 4, looking in the direction of the arrows, and showing how the flattened distal ends of the nails may be compactly disposed contiguous to an incision.

FIG. 5 shows how the flattened ends F of the three nails used in FIG. 4, may be disposed compactly at and adjacent the exterior cortex at the incision. In this way the joint remains free and mobile and the patient's comfort is enhanced. The presence of but one incision and the minimum disturbance or displacement of marrow and cancellous are further advantages.

Figure 14:
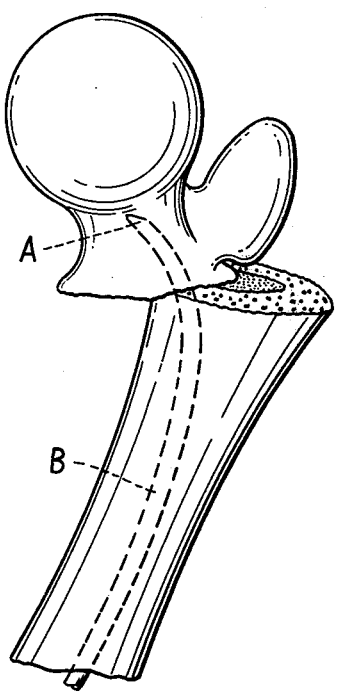
FIG. 14 is a detail view showing a fractured femur with parts laterally displaced and, in dotted lines, the proximal end of a nail embodying the invention, entering the head portion.

Referring to FIG. 14, there is shown the thigh or proximal portion of a fractured femur wherein the parts have been laterally displaced. As the nail is driven upwardly in and along the medullary canal, it is thereby warped or distorted toward a more nearly straight form. Being resilient, the nail is thereby stressed so that its proximal end exerts a lateral or transverse force tending to move the point A radially outwardly. This force enables the surgeon, by proper rotational adjustments of the nail, preferably under X-ray inspection, to direct the point into the canal of the superjacent fragment as is clearly shown by the figure.

Figure 15:
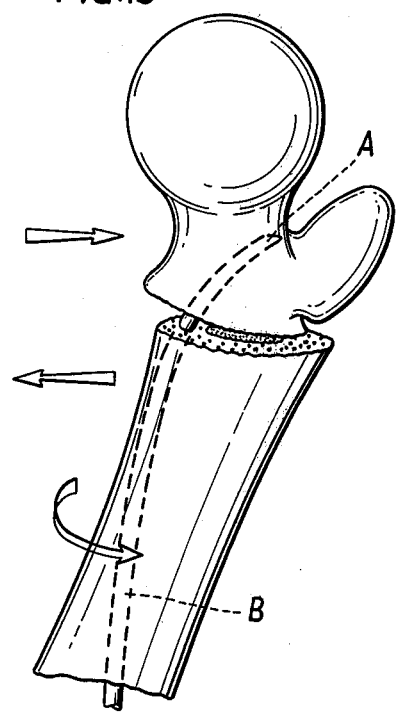
FIG. 15 is a view like FIG. 14 but illustrating how, by angular adjustment or turning of the nail in and with respect to the medullary canal, the head may be adjusted laterally to restore it to normal relation with the subjacent part, as indicated by the arrows.

When end A has been thus directed into the upper fragment, the surgeon can, by rotational adjustment of the nail, as by a set like that shown at FIG. 3, laterally shift the part into normal relation with respect to the subjacent part, as indicated by the arrows, FIG. 15. The control thus afforded is delicate, precise and exact so that satisfactory and accurate healing are promoted and assured. The flexibility of the nail, enabling it to be flexed as it is driven into and along the bone canal, together with its resiliency urging its return to pre-insertion form of shorter radii of curvature, are thus important features of the invention.

Figure 16:
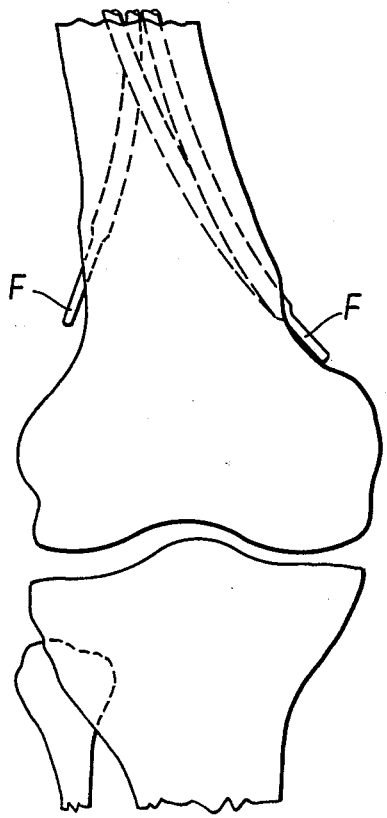
FIG. 16 is a detail view of the lower end of a femur, with a plurality of nails of the invention inserted into incisions and showing how their external distal ends leave unimpaired the articulation with the tibia.
Figure 17:
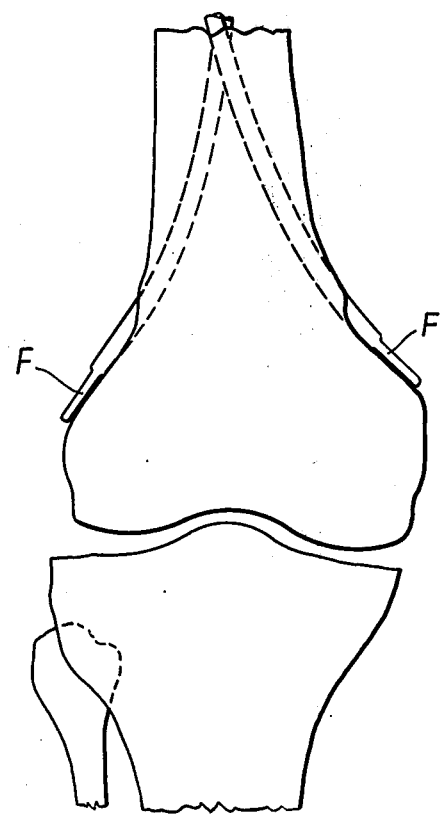
FIG. 17 is a view similar to FIG. 16 but showing other positions which the bent distal ends of emplaced nails may have with respect to the external surface of the femur.

FIGS. 16 and 17 are views of the knee joint, showing contiguous portions of femur, tibia and fibula. In these figures, two incisions have been employed at essentially diametrically opposite locations at the condyle. These figures thus show an additional use for a plurality of nails embodying the invention, in one and the same bone. They also illustrate how the nails, used as intended, leave the joint free and mobile. Thus the need for a cast is obviated, rapid healing is promoted and the comfort of the patient during healing is enhanced.

FIGS. 13a, 13b and 13c illustrate various cross-sectional forms which the nails of the invention may have, such as circular, hexagonal or crescent, respectively. Numerous other cross-sectional forms are possible without affecting the new and useful results possible with the invention.

The internal angle between tangents to the nail of FIG. 1, for instance, at points A and D, will be in the range of about 120° and 135°. The nail is, as in the prior art heretofore made of record, of stainless steel coated with low-friction synthetic plastic such as that sold under the trademark name of "Teflon". Such a coating reduces the forces required for emplacement of the nail or nails, and avoids fretting and/or corrosion otherwise possible with even high grade material. The resiliency, and strength of the metal from which the nails are made, is preferably about 125 to 145 Kp/mm$^2$, which is suitable not only for the optimum manufacture of the nail, but also results in an optimum elasticity and elastic memory without breaking when the bending slightly exceeds the elastic point.

The length of the nail required for any particular operation depends of course upon the linear dimension of the bone itself and the size or effective diameter will to a certain extent, depend upon the diameter of the medullary canal. By "effective diameter" is meant the diameter of a nail circular in cross-section or the cross-sectional area of a nail non-circular in cross section, as in FIGS. 13b and 13c, which possesses the same resistance to bending as if it were circular in section. Thus the diameter for a nail circular in transverse section, may be between about 3 and 6 mm, preferably about 4.5 mm for one intended for an adult male femur in proportion to a length of the nail of between 1:60 to 1:110 and proportionally less for bones of lesser over-all length. Since the femur is the longest bone in the body, the lengths and diameters of nails for use in other bones of the body or of such as of females and children will decrease generally proportionally as, for instance, between 3 and 4 mm. for the humerus and tibia. Since as previously explained, a plurality of nails may be employed in one operation, the actual effective diameter is to be calculated and may, in fact, vary in accordance with the preference of the surgeon. One surgeon might prefer to use a single nail of greater diameter while another might choose to use two or more of lesser diameter. Irrespective of the over-all length the linear extents of the various curved and straight sections or portions of any particular nail the relation or proportions between those portions will remain about the same.

The point formed at the proximal end A is preferably formed to lie in a plane about 45° to the tangent at that point, and has its edges rounded off to enable and assure free and unimpeded passage of this end in and along the canal. As is apparent from FIGS. 1 and 2 the plane of the cut end is essentially normal to the plane of FIG. 1 and in or parallel to the plane of FIG. 2. The stress engendered by emplacement of the nail thus urges the point radially outwardly of the canal, such as to the right as the invention is viewed upon FIG. 1. It is contemplated that the invention may be purveyed in the form of a kit including an assortment of nails of various sizes shapes and lengths for use in connection with at least a plurality of major bones subject to fracture and having medullary canals, together with at least one tool selectively attachable to the distal end of each nail in the package.

Small nails for small bones may require flats of respectively smaller sizes. The kit or assortment includes a corresponding plurality of tools capable of engaging such variously sized flats.

We claim:

1. A curved flexible and resilient nail for repositioning and fixing fragments of bones, which nail comprises, a proximal end, a curved portion extending from said proximal end, a distal end provided with a coupling element adapted to be connected to means for driving the nail, a first straight portion between said coupling element and said curved portion, a first bend between said distal end and said first straight portion, and a second straight portion between said distal end and said first bend.

2. A nail as set forth in claim 1, which comprises, a second bend between said second straight portion and said distal end, and a third straight portion between said second bend and said distal end.

3. A curved flexible resilient nail for repositioning and fixing fragments of bones, which nail comprises, a proximal end, a curved portion extending from said proximal end, a distal end provided with a coupling element adapted to be connected to means for driving the nail, a straight portion between said coupling element and said curved portion, and a second curved portion which is adapted to conform to a femur condyle and is disposed between said straight portion and said distal end.

4. The combination comprising a curved flexible and resilient nail for repositioning and fixing fragments of bones and a nail set for use in driving such nail, said nail having a rear end portion formed with a conical tip and with screw threads, said nail set having a longitudinal bore, which has a first tapped portion adapted to threadedly engage said screw threads of said nail, and a second tapped portion axially spaced from said first tapped portion, said nail set comprising an Allen-head screw screwed into said second tapped portion, and a cylindrical member disposed in said longitudinal bore and engaging said Allen-head screw and said rear end portion of said nail and non-rotatably connecting the latter to said nail set.

5. An elongated surgical nail of flexible resilient material, having a proximal end and a distal end, said nail having an arcuately curved portion extending from said proximal end to a first point about one-third to one-half the over-all length of the nail, and a generally straight portion extending from said first point to said distal end.

6. The nail of claim 5, the radius of curvature of said arcuately curved portion increasing gradually from said proximal end to said first point.

7. The nail of claim 5, the tangents to the nail at said proximal end and said first point, respectively, making an angle of about 120° to 135°.

8. The nail of claim 7, said material being stainless steel rod of generally constant diameter throughout its length, said diameter being between about 3 and 6 mm for a femur, preferably about 4.5 mm in proportion to a length of the nail between 1:60 to 1:110 and proportionately less for bones of lesser over-all lengths.

9. The nail of claim 7, said material being stainless steel rod of generally constant diameter from said distal end to said first point, and of gradually decreasing diameter from said first point to said distal end.

10. The nail of claim 8, said distal end terminating in first means for detachable securement thereto, of a set for driving said nail into and extracting it from, the medullary canal, and operable to effect angular adjustment thereof, in and relatively to the bone.

11. The nail of claim 10, said first means comprising a flat formed integrally with said nail and lying in a plane including the longitudinal axis of the contiguous portion of the nail, there being an aperture in and extending transversely through said flat.

12. The nail of claim 5, said nail being arcuately curved in a first plane only, through the longitudinal axis of said straight portion.

13. The nail of claim 12, said nail being arcuately curved in a second plane through said axis, angular to said first plane.

14. The nail of claim 13, said nail being curved in one direction in said second plane, from said first point to said proximal end, and curved in a different direction in said second plane, from a second point at the terminus of said straight section nearest said distal end, the angles between the longitudinal axis of said straight section, extended, and the tangents to said curved sections at the respective ends of the nail, being in the range about 5° to 20°.

15. The combination with the nail of claim 11, a shank having a recess in a first terminal end, to non-rotatably fit over and about said flat, and a driving head fixed with the other terminal end of said shank.

16. The combination of claim 15, lever means pivoted on said shank and having an offset end forming a nose, said lever means being pivotable from a first position wherein said nose extends through said aperture, to releasably hold said nail and shank together, with said flat disposed in said recess, and a second position releasing said flat for movement out of said recess.

17. The combination of claim 16, and means yieldingly urging said lever into first position.

18. The nail of claim 10, said first means comprising a U-shaped bend terminating the distal end of said nail.

19. The combination of claim 16, further comprising:
an assortment of at least one of said nails, each arcuately curved in several planes and in several diameters relative their over-all length to proportionally sized said flats.

20. The combination of claim 19 further comprising:
at least one set for driving each said nail of different diameters, lengths and sizes and of flats for extracting them from the said bones.

21. The nail of claim 8, having the elasticity of metal between about 125 Kp/mm$^2$ to 145 Kp/mm$^2$.

22. The nail of claim 7, of a length between 32 to 49 cm in proportion to a diameter of about 3 to 6 mm for a femur, respectively, preferably about 4.5 mm.

23. The nail of claim 1,
said coupling element at the distal end being flat to permit a fish-scale type mating overlying with the distal ends of a plurality of other similarly shaped nails when protruding in situ through the incision in the bone.

24. The nail of claim 23,
said flat being enlarged relativ to the shank and for adjustment of the nail through the medullary canal.

* * * * *